(12) United States Patent
Torii

(10) Patent No.: US 6,582,360 B1
(45) Date of Patent: *Jun. 24, 2003

(54) TUBE CONNECTION STRUCTURE IN ENDOSCOPE

(75) Inventor: Yuichi Torii, Omiya (JP)

(73) Assignee: Fuji Photo Optical Co., Ltd., Omiya (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/571,252
(22) Filed: May 16, 2000

(30) Foreign Application Priority Data

May 19, 1999  (JP) .......................... 11-138357

(51) Int. Cl.[7] .................................. A61B 1/00
(52) U.S. Cl. ...................... 600/129; 600/127; 600/130; 600/156
(58) Field of Search ............... 600/129, 127, 600/109, 130, 160, 156, 158

(56) References Cited

U.S. PATENT DOCUMENTS

| | | | | |
|---|---|---|---|---|
| 4,706,653 A | * | 11/1987 | Yamamoto | 600/127 |
| 4,773,396 A | * | 9/1988 | Okazaki | 348/65 |
| 4,779,130 A | * | 10/1988 | Yabe | 348/76 |
| 4,832,003 A | * | 5/1989 | Yabe | 348/65 |
| 4,881,810 A | * | 11/1989 | Hasegawa | 356/241.5 |
| 5,154,164 A | * | 10/1992 | Chikama | 126/6 |
| 5,275,152 A | * | 1/1994 | Krauter et al. | 138/109 |
| 5,291,010 A | * | 3/1994 | Tsuji | 250/208.1 |
| 5,454,366 A | * | 10/1995 | Ito et al. | 600/109 |
| 5,483,951 A | * | 1/1996 | Frassica et al. | 600/104 |
| 5,486,154 A | * | 1/1996 | Kelleher | 600/104 |
| 5,643,175 A | * | 7/1997 | Adair | 600/123 |
| 5,685,823 A | * | 11/1997 | Ito et al. | 600/121 |
| 5,733,243 A | * | 3/1998 | Yabe et al. | 600/121 |
| 5,746,695 A | * | 5/1998 | Yasui et al. | 600/121 |

FOREIGN PATENT DOCUMENTS

JP    Y2-2-10494    3/1990

\* cited by examiner

Primary Examiner—Linda C. M. Dvorak
Assistant Examiner—Jocelyn Ram
(74) Attorney, Agent, or Firm—Oliff & Berridge, PLC

(57) ABSTRACT

A tip component is provided at an extremity of an insertion part of an endoscope. The tip component includes a body member, in which a forceps aperture is formed. A forceps tube is arranged inside the insertion part. A hard part is formed at the end of the forceps tube, at which the forceps tube is sandwiched between an inner cylinder and an outer cylinder. The hard part is inserted into the forceps aperture of the body of the tip component and is fixed with a screw. A connecting part between the forceps tube and the forceps aperture is thus formed in the body of the tip component, and the length of the tip component is reduced as a result.

5 Claims, 4 Drawing Sheets

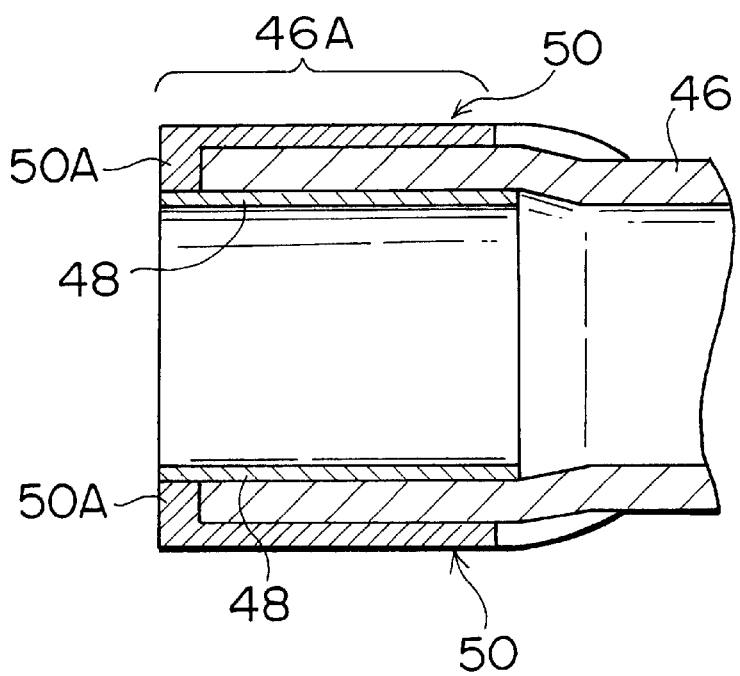
F I G. 3
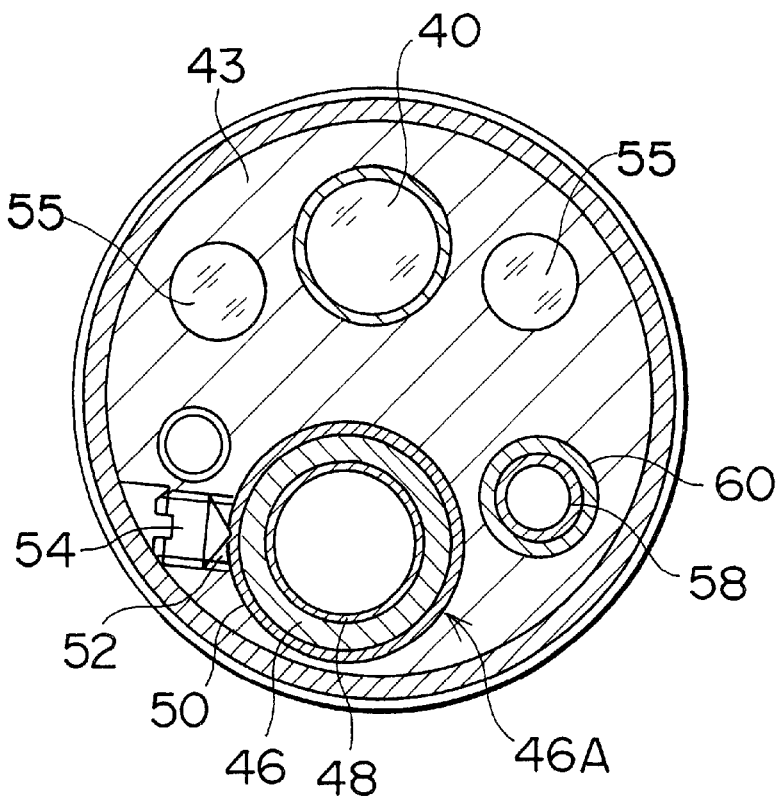
F I G. 4

TUBE CONNECTION STRUCTURE IN ENDOSCOPE

BACKGROUND OF THE INVENTION

1. Field of the Invention

This invention relates to a tube connection structure in an endoscope, particularly to a tube connection structure for connecting a forceps tube arranged in an endoscope insertion part with a forceps aperture formed in a tip component of the endoscope insertion part.

2. Description of Related Art

A tip component is provided at the extremity of a curved part of an endoscope insertion part. Japanese Utility Model Publication No. 2-10494 discloses the tip component, in which a charge coupled device (CCD) 2 is arranged and a forceps aperture 3 is formed as shown in FIG. 5. Treatment equipment such as forceps is inserted and extracted through the forceps aperture 3. The forceps aperture 3 is connected to a rubber forceps tube 4 through a metal forceps tube 5, which is inflexible. The metal forceps tube 5 is disposed in close proximity to a CCD board 6 in order to achieve a small diameter of the tip component 1. For this reason, the rubber forceps tube 4 is connected with the metal forceps tube 5 at a position behind the CCD board 6.

The conventional tube connection structure, however, has such a disadvantage that a tip section ring 7 for protecting the CCD board 6 and the forceps tube 5 must be long in order to cover both the CCD board 6 and the inflexible forceps tube 5, which extends up to the position behind the CCD board 6. Therefore, the tip component 1 must be long, and an observation window 8 of the tip component 1 has a narrow observation range due to a limitation on the curve angle of the endoscope curved part.

SUMMARY OF THE INVENTION

It is therefore an object of the present invention to provide a tube connection structure in an endoscope that reduces the length of the tip component.

The above object can be accomplished by providing an insertion part of an endoscope, comprising: a tip component provided at an extremity of the insertion part, the tip component including a body member having an aperture part; and a tube member arranged inside the insertion part, an end of the tube member being connected with the aperture part, wherein a connecting part between the aperture part and the end of the tube member is formed in the body member.

According to the present invention, the connecting part between the tube member and the aperture part is formed in the body of the tip component, which was an unused space in the prior art. This reduces the length of the tip component.

The above object can be accomplished by providing an insertion part of an endoscope, comprising: a tip component provided at an extremity of the insertion part, the tip component including a body member having an aperture part; a tube member arranged inside the insertion part, an end of the tube member being connected with the aperture part; and an imaging device board on which an imaging device is mounted, the imaging device board being arranged inside the tip component, wherein a connecting part between the aperture part and the end of the tube member is arranged closer to an extremity of the tip component than the imaging device board.

According to the present invention, the connecting part between the tube member and the aperture part is arranged closer to the extremity of the tip component than the imaging device board disposed inside the tip component part. The curving of the curved part is restricted at a rear end of the imaging device board, not at the connecting part. Therefore, the curved part is curved at a wide angle.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 3 is a longitudinal sectional view of a hard part of a forceps tube in FIG. 2;

FIG. 4 is a cross-sectional view taken along line 4—4 of the tip component in FIG. 2.

DETAILED DESCRIPTION OF THE PREFERRED EMBODIMENT

A preferred embodiment of a tube connection structure in an endoscope according to the present invention will be described in detail below with reference to the accompanying drawings.

Figure 1:
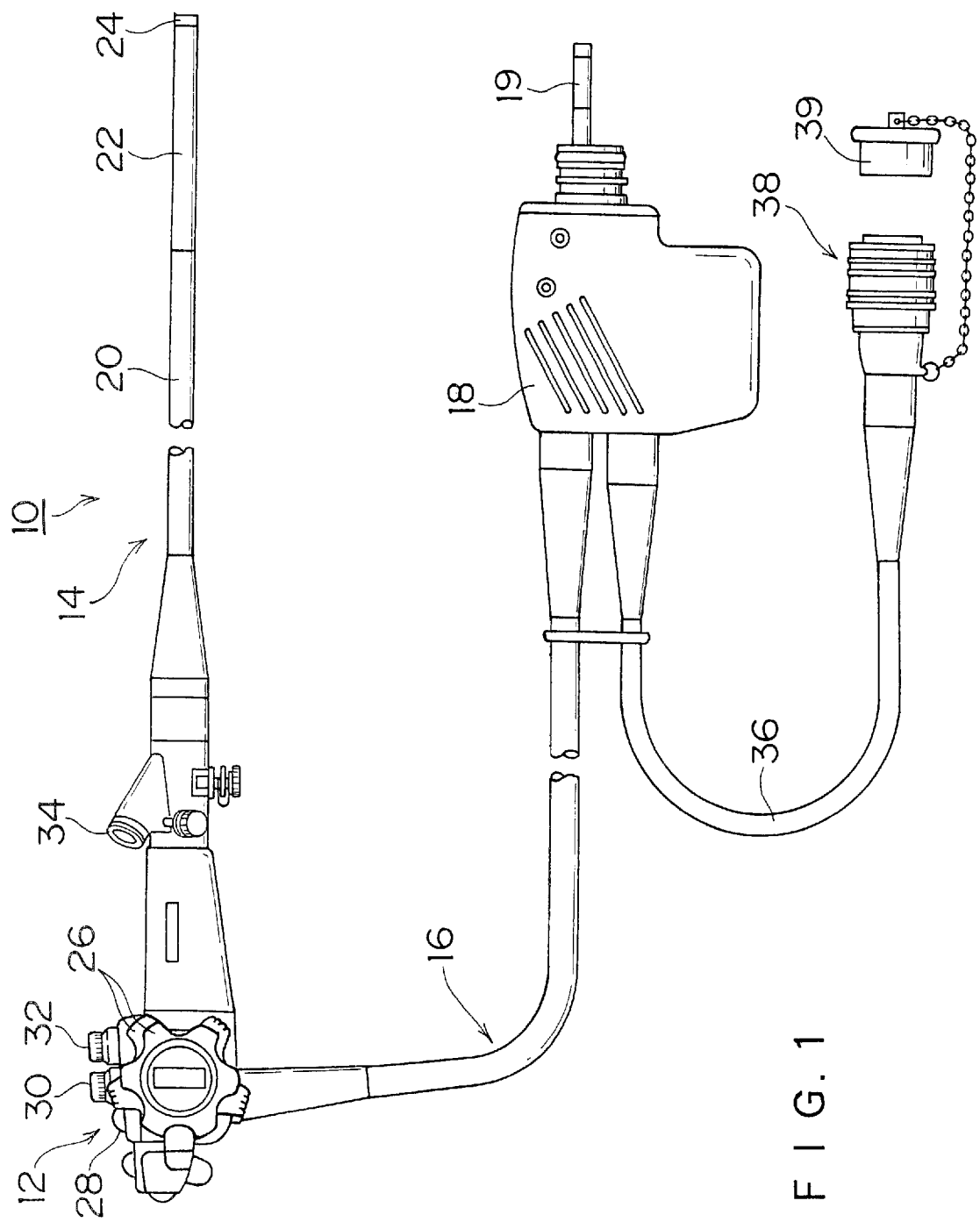
FIG. 1 is a view showing the entire structure of an endoscope to which a tube connection structure in an endoscope according to the present invention.

As shown in FIG. 1, an electronic endoscope 10 with a tube connection structure according to an embodiment of the present invention has a manual control part 12 and an insertion part 14 connected with the manual control part 12. The insertion part 14 comprises a soft part 20, a curved part 22 and a tip component 24. The curved part 22 is remotely curved by rotating a pair of knobs 26 for curve control, which are provided at the manual control part 12, so that the tip component 24 can be pointed to a desired direction.

The manual control part 12 has a forceps insertion aperture 34, through which treatment equipment such as forceps is inserted. The manual control part 12 also has a shutter button 28, a suction button 30 and an air/water supply button 32. The manual control part 12 is connected with a light guide (LG) connector 18 through an LG soft part 16. The LG connector 18 has a light guide bar 19 connected to a light source device (not shown), and connects to an electric connector 38 through a flexible tube 36. A cap 39 is provided to cover the electric connector 38.

Figure 2:
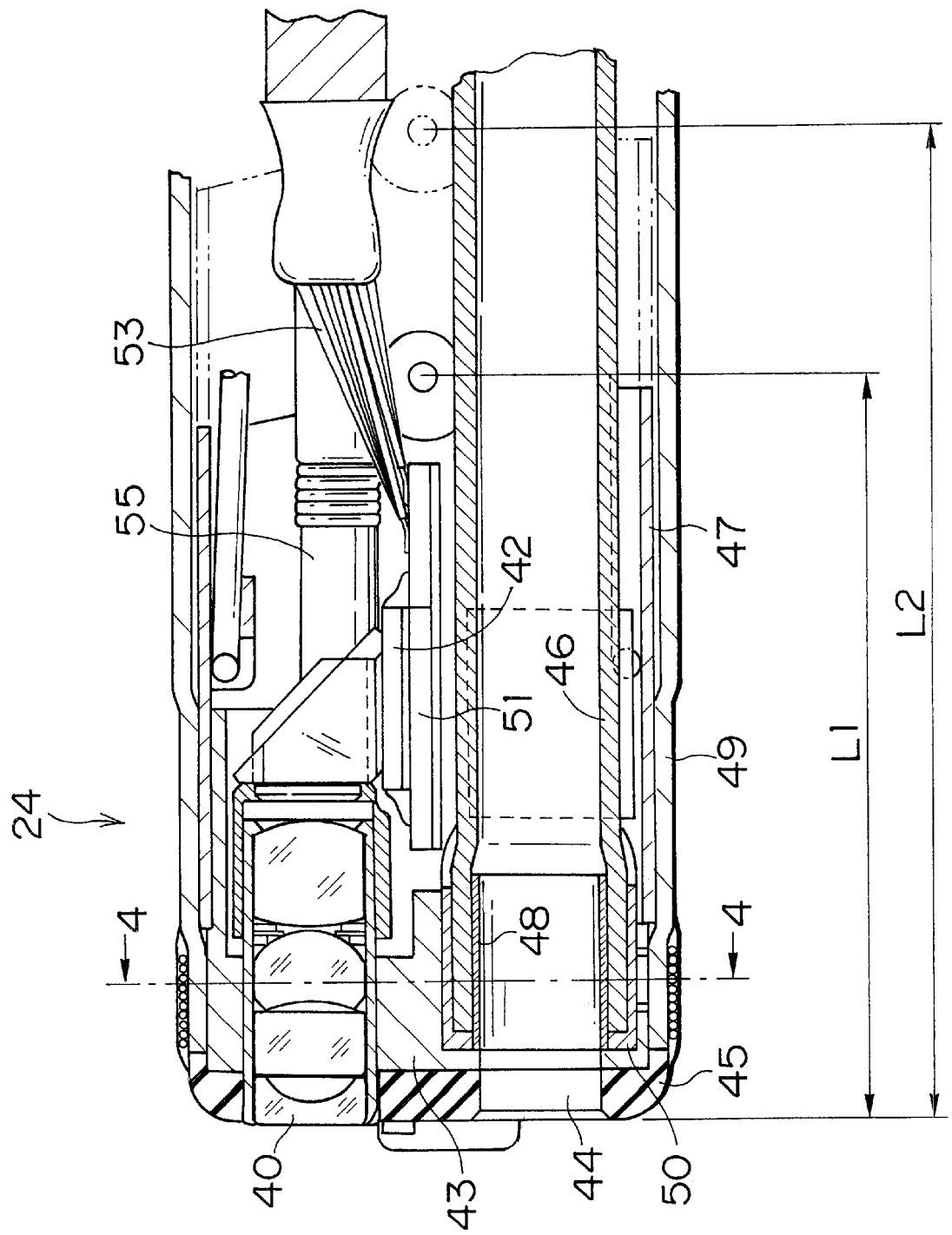
FIG. 2 is a longitudinal sectional view of a tip component in FIG. 1.

As shown in FIG. 2, the tip component 24 comprises a body 43 and a cap 45. The tip component body 43 is connected with a cylindrical tip section ring 47, and an inflexible part L1 including the tip section ring 47 is formed as the tip component 24. The tip component body 43 and the tip section ring 47 are covered with an outer covering tube 49, and the cap 45 made of plastic is attached to an end of the tip component body 43.

An objective lens 40 is disposed on an end face of the tip component 24. A charge-coupled device (CCD) 42 supported by a board 51 is provided behind the objective lens 40. An observed image captured through the objective lens 40 is formed on a light-receiving surface of the CCD 42. The CCD 42 converts the observed image into electric signals, which are outputted through a signal cable 53 connected with the board 51 and through the electric connector 38 in FIG. 1 to a processor (not shown). The electric signals outputted to the processor are converted by a signal processing circuit into video signals, which are then outputted to a monitor (not shown). A light guide 55 in FIG. 2 is connected with the light guide bar 19 in FIG. 1. When the light guide bar 19 is connected to the light source device (not shown), illumination light from the light source device is transmitted through the light guide 55 and is then projected through an objective lens (not shown) disposed at the tip component 24.

As shown in FIG. 2, an aperture part or a forceps aperture 44 is formed in the tip component body 43 in the axial direction of the tip component 24. The forceps aperture 44 is connected with the forceps insertion aperture 34 in FIG. 1 through a tube member or a forceps tube 46. The treatment equipment such as the forceps is inserted and extracted through the forceps insertion aperture 34.

As shown in FIG. 3, a hard part 46A is formed at an end of the forceps tube 46 by fitting an inner cylinder 48 inside the forceps tube 46 and fitting an outer cylinder 50 outside the inner cylinder 48. A projection part 50A is formed at the end of an inner peripheral surface of the outer cylinder 50, and the projection part 50A is in contact with an outer peripheral surface of the inner cylinder 48. The outer cylinder 50 and the inner cylinder 48, and the outer cylinder 50 and the forceps tube 46 are adhered by an epoxy adhesive agent or the like. Consequently, the hard part 46A, in which the forceps tube 46 is sandwiched between the inner cylinder 48 and the outer cylinder 50, is formed at the end of the forceps tube 46.

The hard part 46A is fitted into the forceps aperture 44 of the tip component body 43 as shown in FIG. 2, and is adhered to the tip component body 43 with the epoxy adhesive agent or the like. Then, as shown in FIG. 4, the hard part 46A is securely fixed to the tip component 24 by fastening a screw 54 engaged with a screw hole 52, which is formed in the tip component body 43 perpendicularly to the forceps aperture 44.

There will now be explained the operation of the tube connection structure that is constructed in the above-mentioned manner.

Figure 5:
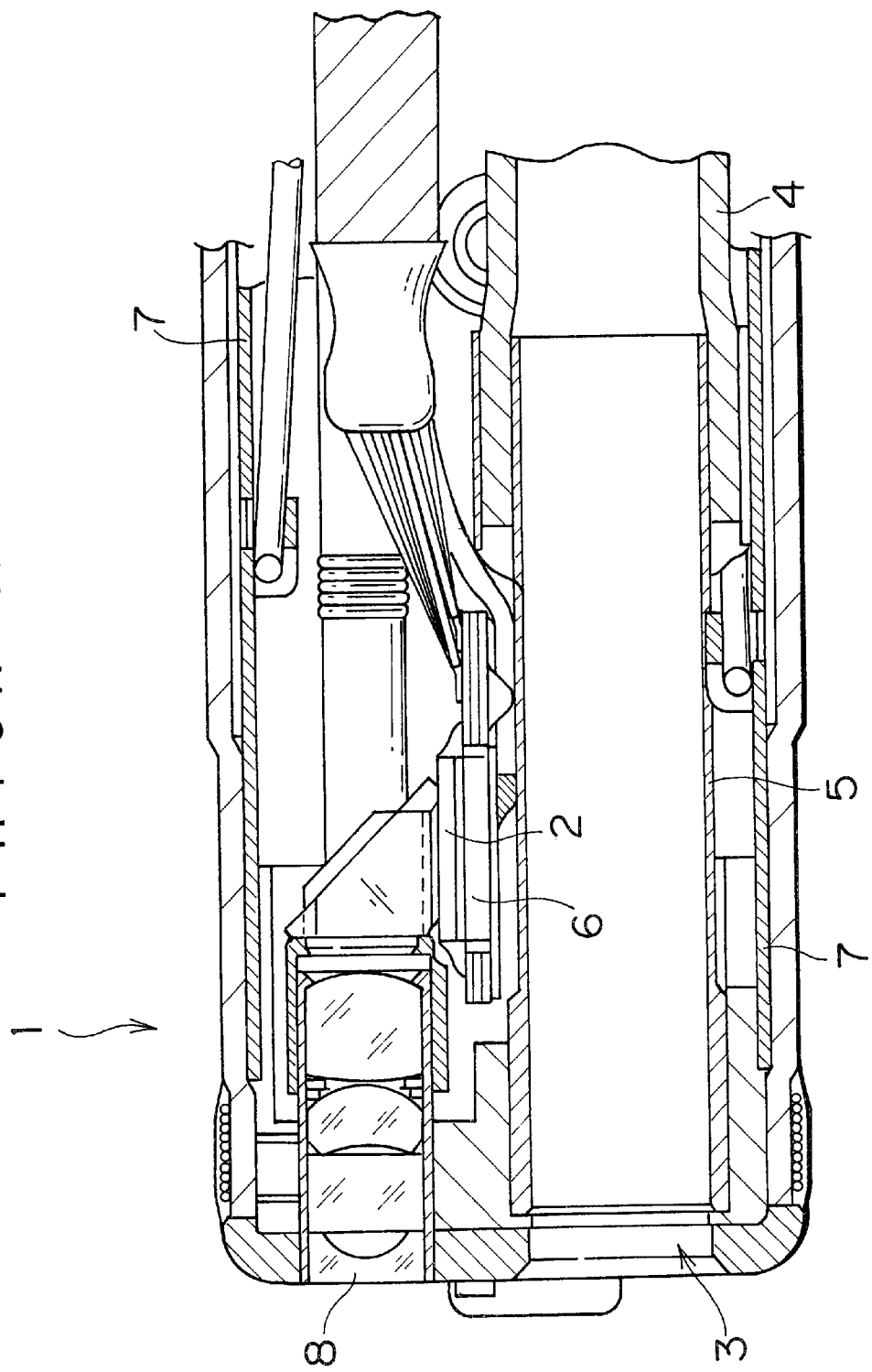
FIG. 5 is a sectional view showing a conventional tube connection structure in an endoscope.

A connecting part between the forceps tube 46 and the forceps aperture 44 is formed in the body 43 of the tip component 24, and is positioned closer to the end of the tip component 24 than the board 51 of the CCD 42. Thus, the CCD board 51 is located at the closest position to the manual control part 12 among inflexible members arranged inside the tip component 24. Therefore, an inflexible part in the present embodiment is shorter compared with the prior art in FIG. 5 wherein the metal forceps tube 5 extends closer to the manual control part than the CCD board 6. Hence, a length L1 of the tip component 24 of the present embodiment is smaller than a length L2 in the prior art.

In the tube connection structure of the present embodiment, the hard part 46A is formed at the end of the forceps tube 46 and is directly fitted into the forceps aperture 44, so that the connecting part between the forceps tube 46 and the forceps aperture 44 can be formed in the tip component body 43. This reduces the length of the tip component 24.

In the tube connection structure of the present embodiment, the outer cylinder 50 is securely fixed to the body 43 of the tip component 24 through the screw 54, and this prevents the forceps tube 46 from falling off the body 43 of the tip component 24.

In the tube connection structure of the present embodiment, there is provided no metal forceps tube, and the number of inflexible members arranged inside the tip component 24 is thus reduced. This enables a free arrangement of the members inside the tip component 24. Therefore, the tip component 24 can be made thinner by, for example, shifting the forceps aperture 44 toward a central axis of the tip component 24.

In the above-described embodiment, the tube connection structure of the present invention is applied to the connecting part between the forceps tube 46 and the forceps aperture 44, but the present invention should not be restricted to this. For example, the same effects can be achieved by applying the tube connection structure of the present invention to a connecting part between the air/water supply aperture 58 and the air/water supply tube 60 in FIG. 4.

In the above-described embodiment, the hard part 46A is formed by sandwiching the end of the forceps tube 46 between the inner cylinder 48 and the outer cylinder 50. The present invention, however, should not be restricted to this. For example, the hard part 46A may be formed by hardening the end of the forceps tube 46 by heat, a chemical agent, or the like.

In the above-described embodiment, the hard part 46A is securely fixed to the body 43 of the tip component 24 through the screw 54. The present invention, however, should not be restricted to this on condition that the hard part 46A is firmly connected with the tip component 24. For example, a projection part composed of an elastic body may be formed on the outer peripheral surface of the outer cylinder 50, and a recess part engaged with the projection part may be formed on the inner peripheral face of the forceps aperture 44. In this case, the forceps tube 46 can be snappingly connected to the forceps aperture 44.

Moreover, the inner cylinder 48 and the outer cylinder 50 may be unitedly formed with the body 43 of the tip component 24. In this case, the end of the forceps tube 46 is inserted into a space between the inner cylinder 48 and the outer cylinder 50, and then the forceps tube 46 is fixed by fastening the screw 54.

In the above-described embodiment, the connecting part between the forceps tube 46 and the forceps aperture 44 is formed in the body 43 of the tip component 24. The present invention, however, should not be restricted to this on condition that the connecting part is arranged closer to the end of the tip component 24 than the CCD board 51. This achieves the same effects as the above-described embodiment.

In the above-described embodiment, the tube connection structure of the present invention is applied to the electronic endoscope, but the present invention should not be restricted to this. The tube connection structure of the present invention may be applied to various kinds of endoscopes in that the aperture and the tube member are connected at the tip of the endoscope insertion part.

As set forth hereinabove, according to the tube connection structure in the endoscope of the present invention, the connecting part between the tube member and the aperture is formed in the tip component body, and thereby the connecting part, which caused the tip component to be long in the prior art, is shifted closer to the end of the tip component, so that the length of the tip component is reduced.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An insertion part of an endoscope comprising:
   a tip component provided at an extremity of the insertion part, the tip component including an outer covering tube, a tip section ring inside the outer covering tube and a body member having an aperture part;
   one of a forceps tube and an air/water supply tube arranged inside the insertion part, an end of the one of the forceps tube and the air/water supply tube being connected with the aperture part,
   wherein a connecting part between the aperture part and the end of the one of the forceps tube and the air/water supply tube is formed in the body member;
   an inner cylinder fitted inside the end of the one of the forceps tube and the air/water supply tube; and
   an outer cylinder fitted outside the end of the one of the forceps tube and the air/water supply tube,
   wherein the one of the forceps tube and the air/water supply tube at the connecting part is sandwiched between the inner cylinder and the outer cylinder, the one of the forceps tube and the air/water supply tube at the connecting part being inserted in the aperture part in the body.

2. The insertion part of an endoscope as claimed in claim 1, further comprising a CCD board on which an imaging device is mounted, the CCD board being arranged inside the tip component, wherein the tube at the connecting point is positioned closer to the tip component than the CCD board.

3. The insertion part of an endoscope as claimed in claim 1, further comprising a projection part formed at an end of an inner peripheral surface of the outer cylinder.

4. An insertion part of an endoscope comprising:
   a tip component provided at an extremity of the insertion part, the tip component including a body member having an aperture part;
   one of a forceps tube and an air/water supply tube arranged inside the insertion part, an end of the tube being connected with the aperture part,
   wherein a connecting part between the aperture part and the end of the tube is formed in the body member;
   an inner cylinder fitted inside the end of the tube; and
   an outer cylinder fitted outside the end of the tube, the outer cylinder being fitted in the aperture part in the body member and having a projection part at an end of an inner peripheral surface and forming an abutment part,
   wherein the tube at the connecting part is sandwiched between the inner cylinder and the outer cylinder, and abuts the abutment part.

5. The insertion point of an endoscope according to claim 4, wherein the projection part is L-shaped in cross-section.

* * * * *